United States Patent
Shan et al.

(12) 
(10) Patent No.: US 8,460,891 B2
(45) Date of Patent: Jun. 11, 2013

(54) MONOCLONAL ANTIBODIES DETECTION METHODS FOR ENZYMES THAT CONFER RESISTANCE TO 2,4-DICHLOROPHENOXYACETIC ACID IN PLANTS

(75) Inventors: Guomin Shan, Carmel, IN (US); Gaofeng Lin, Zionsville, IN (US); Joelene K. Smith Drake, Avon, IN (US); Marcelo Sosa, Zionsville, IN (US)

(73) Assignee: Dow Agrosciences LLC., Indianapolis, IN (US)

( * ) Notice: Subject to any disclaimer, the term of this patent is extended or adjusted under 35 U.S.C. 154(b) by 174 days.

(21) Appl. No.: 13/151,389

(22) Filed: Jun. 2, 2011

(65) Prior Publication Data
US 2011/0300556 A1 Dec. 8, 2011

Related U.S. Application Data

(60) Provisional application No. 61/351,593, filed on Jun. 4, 2010.

(51) Int. Cl.
*G01N 33/573* (2006.01)
*G01N 33/53* (2006.01)
*C12N 5/12* (2006.01)
*C07K 16/16* (2006.01)

(52) U.S. Cl.
USPC ............ 435/7.4; 435/7.1; 435/7.94; 435/338; 530/388.1

(58) Field of Classification Search
None
See application file for complete search history.

(56) References Cited

U.S. PATENT DOCUMENTS

| 6,153,401 A | 11/2000 | Streber et al. |
| 2009/0093366 A1 | 4/2009 | Wright et al. |
| 2011/0203017 A1* | 8/2011 | Wright et al. ................. 800/298 |

FOREIGN PATENT DOCUMENTS

| WO | WO 2007/053482 | 5/2007 |
| WO | WO 2008/141154 | 11/2008 |
| WO | WO 2012/036870 | 3/2012 |

OTHER PUBLICATIONS

Wright et al. "Robust crop resistance to broadleaf and grass herbicides provided by aryloxyalkanoate dioxygenase transgenes" Proc Natl Acad Sci U S A. 107(47), pp. 20240-20245 and accompanying 3 pages of Online Supplementary Material; Published online before print Nov. 8, 2010.*
Database Genbank, Accession No. M16730, Streber, W.R. et al. "Analysis, cloning, and high-level expression of 2,4-dichlorophenoxyacetate monooxygenase gene tfdA of *Alcaligenes eutrophus* JMP134" Apr. 26, 1993, pp. 1-2.
Written Opinion in International Application No. PCT/US2011/038848, Jan. 17, 2012, pp. 1-3.

* cited by examiner

*Primary Examiner* — Christine Foster
(74) *Attorney, Agent, or Firm* — Ronald S. Maciak; Saliwanchik, Lloyd & Eisenschenk

(57) ABSTRACT

Described herein are monoclonal antibodies and methods useful for determining and quantitating the presence of an aryloxyalkanoate dioxygenase enzyme.

15 Claims, No Drawings

MONOCLONAL ANTIBODIES DETECTION METHODS FOR ENZYMES THAT CONFER RESISTANCE TO 2,4-DICHLOROPHENOXYACETIC ACID IN PLANTS

CROSS-REFERENCE TO RELATED APPLICATION

This application claims the benefit of U.S. Provisional Patent Application 61/351,593, filed Jun. 4, 2010, the disclosure of which is hereby incorporated by reference in its entirety.

BACKGROUND OF THE INVENTION 2,4-dichlorophenoxyacetic acid (2,4-D) is in the phenoxy acid class of herbicides and has been used in many monocot crops such as corn, wheat, and rice for the selective control of broadleaf weeds without severely damaging the desired crop plants. 2,4-D is a synthetic auxin derivative that acts to deregulate normal cell-hormone homeostasis and impede balanced, controlled growth; however, the exact mode of action of this class of herbicides is still not fully understood. Triclopyr and fluroxypyr are pyridyloxyacetic acid herbicides that also act as a synthetic auxin.

These herbicides have different levels of selectivity on certain plants (e.g., dicots are more sensitive than monocots). Differential metabolism by different plants is one explanation for varying levels of selectivity. In general, plants metabolize 2,4-D slowly, so varying plant response to 2,4-D may be more likely explained by different activity at the target sites (WSSA, 2002; Herbicide Handbook 8$^{th}$ edition; Weed Science Society of America; Lawrence, Kans. pp. 492.) Plant metabolism of 2,4-D typically occurs via a two-phase mechanism, typically hydroxylation followed by conjugation with amino acids or glucose (WSSA, 2002).

Over time, certain microbial populations challenged with 2,4-D have developed an alternate pathway for degrading this xenobiotic that results in the complete mineralization of 2,4-D. Successive applications of the herbicide select for microbes that can utilize the herbicide as a carbon and energy source for growth, giving them a competitive advantage in the soil. For this reason, currently formulated 2,4-D has a relatively short soil half-life and no significant carryover effects on subsequent crops.

One organism that has been extensively researched for its ability to degrade 2,4-D is *Ralstonia eutropha* (Streber, et al; 1987; Analysis, cloning, and high-level expression of 2,4-dichlorophenixyacetic monooxygenase gene tfdA of *Alcaligenes eutrophus* JMP134. J. Bacteriol. 169:2950-2955). The gene encoding the enzyme in the initial step of the mineralization pathway is tfdA. See U.S. Pat. No. 6,153,401 and GENBANK Acc. No. M16730. The TfdA gene product catalyzes the conversion of 2,4-D to dichlorophenol (DCP) via an α-ketoglutarate-dependent dioxygenase reaction (Smejkal; et al.; 2001. Substrate specificity of chlorophenoxyalkanoic acid-degrading bacteria is not dependent upon phylogenetically related tfdA gene types. Biol. Fertil. Sols 33:507-513). DCP has little herbicidal activity compared to 2,4-D. TfdA has been used in transgenic plants to impart 2,4-D resistance in dicot plants such as cotton and tobacco which naturally sensitive to 2,4-D (Streber; et al.; 1989. Transgenic tobacco plants expressing a bacterial detoxifying enzyme are resistant to 2,4-D. Bio/Technology 7:811-816.), and U.S. Pat. No. 5,608,147).

A large number of tfdA-type genes that encode enzymes capable of degrading 2,4-D have been isolated from soil bacterial and their sequences deposited into the Genbank database. Many homologues of tfdA (>85% amino acid identity) have similar enzymatic properties to tfdA. However, there are a number of homologues that have a significantly lower identity to tfdA (25-50%), yet have the characteristic residues associated with α-ketoglutarate dioxygenase Fe$^{+2}$ dioxygenases. It is therefore not obvious what the substrate specificities of these divergent dioxygenases are.

One unique example with low homology to tfdA (31% amino acid identity) is sdpA from *Delftia acidovorans* (Kohler, H. P. E. 1999; *Delftia acidovorans* MH: a versatile phenoxyalkanoic acid herbicide degrader; J. Ind Microbiol and Biotech. 23:336-340. Westendorf, et al.; 2002. The two enantiospecific dichlorprop/α-ketoglutarate-dioxygenases from *Delfia acidovorans* MC1-protein and sequence data of Rdpa and SdpA. Microbiol. Res. 157:317-22.). This enzyme has been shown to catalyze the first step in (S)-dichlorprop (and other (S)-phenoxypropionic acids) as well as 2,4-D (a phenoxyacetic acid) mineralization (Westendorfet et al.; 2003. Purification and characterization of the enantiospecific dioxygenases from *Delftia acidovorans* MC1 initiating the degradation of phenoxypropionates and phenoxyacetate herbicides. Acta Biotechnol. 23: 3-17).

A plant codon-optimized aryloxyalkanoate dioxygenase gene, AAD-12, that encodes the enzyme originally isolated from *Delftia acidovorans* was first describe for use as a herbicide resistance trait in WO 2007/053482, herein incorporated by reference. The trait confers tolerance to 2,4-D and to pyridyloxyacetate herbicides. The first report of transformed soybeans bearing the AAD-12 gene was in U.S. Provisional Patent Application No. 61/263,950, herein incorporated by reference.

Companies which develop and market recombinant DNA traits for planting seed products formulate, implement and adhere to strict product stewardship plans. These stewardship plans require the use of validated quantitative and qualitative protein detection methods for the recombinant trait to track trait introgression and seed production activities, as well as monitoring grain harvest for the trait. These detection methods must be facile and robust enough to use under GLP and non-GLP conditions. Moreover the methods must be user friendly enough to be easily employed by farmers in the field, grain dealers at the silo, and customs officials at the borders. Therefore, robust, high quality, user friendly protein detection methods and commercial kits are useful and necessary.

While immunoassays are well-known in the art, developing a robust, high quality, validated ELISA (enzyme-linked immunosorbent assays) methods that are reproducibly able to detect a particular transgenic product in an array of plant tissue in both lab and field settings is neither trivial nor routine. Still more challenging is to find antibody pairs that are particularly suited to the development of a lateral flow strip ELISA for detecting an AAD-12 transgenic event.

SUMMARY OF THE INVENTION

The present invention provides a panel of monoclonal antibodies (mAbs) and the hybridoma cell lines that produce. The lines were deposited with the American Type Culture Collection in accordance with the terms of the Budapest Treaty. These mAbs are surprisingly well suited for detecting an AAD-12 transgenic event gene product in a variety of plants and plant tissues. The invention further provides quantitative and qualitative immunoassays using the immunoglobulins of the invention.

DETAILED DESCRIPTION

The present invention encompasses antibodies reactive with AAD-12 and the hybridomas that produce the mAbs. The table below lists the hybridoma line designations and their corresponding ATCC deposit designations.

| Hybridoma/mAb Designation | ATCC Deposit Designation | ATCC Deposit Date |
|---|---|---|
| 539B181.2 | PTA-10919 | 5 May 2010 |
| 539B470.2 | PTA-10920 | 5 May 2010 |
| 539B498.2 | PTA-10921 | 5 May 2010 |
| 539B304.2 | PTA-10922 | 5 May 2010 |
| 539B478.2 | PTA-10923 | 5 May 2010 |

The invention also include methods of using the mAbs for isolating or detecting AAD-12 comprising: a) immobilizing said antibody onto a surface; b) contacting said immobilized antibody with a mixture containing AAD-12; c) separating said immobilized antibody bound to AAD-12 from said mixture; and d) recovering AAD-12 by removing the antibody-bound AAD-12 from said immobilized antibody.

The invention also includes a method of using the claimed antibodies for identifying the presence of AAD-12 in a biological sample comprising: a) immobilizing said antibody onto an assay surface; b) contacting said assay surface with a liquid suspected of containing AAD-12 and washing said assay surface with a suitable solution; c) contacting said assay surface with an anti-AAD-12 antibody labeled with a reporting group and washing said assay surface with a suitable solution; d) detecting the presence of said reporting group.

The invention further includes an analytical method for the quantitative determination of AAD-12 enzyme expressed in transgenic plants, especially soybean and cotton plants. The AAD-12 protein is extracted from soybean samples with a PBS (phosphate buffered saline) solution. The extract is centrifuged; the aqueous supernatant is collected and diluted. An aliquot of the diluted sample is incubated with enzyme-conjugated anti-AAD-12 monoclonal antibody in the wells of an anti-AAD-12 polyclonal or monoclonal antibody-coated plate in a sandwich ELISA format. Both antibodies in the sandwich pair capture the AAD-12 protein in the sample. At the end of the incubation period, the unbound reagents are removed from the plate by washing with PBS. The presence of AAD-12 is detected by incubating the enzyme conjugate with an enzyme substrate, generating a colored product. Since the AAD-12 is bound in the antibody sandwich, the level of color development is proportional to the concentration of AAD-12 in the sample (i.e., lower protein concentrations result in lower color development). The absorbance at 450 nm minus absorbance at a reference wavelength (such as 650 nm) is measured using a plate reader. A calibration curve is estimated from 7 standard concentrations using a quadratic regression equation. This AAD-12 ELISA is specific and sensitive enough for the quantitation of AAD-12 in plant tissue sample extracts. In addition the antibodies of the invention may be used to confirm the presence of AAD-12 using a standard western blotting procedure.

The preparation of antibodies against proteins of interest is well known in the art. See Galfre and Milstein, Methods in Enzymology, Vol. 73, Academic Press, New York (1981); James W. Goding, Monoclonal Antibodies: Principles and Practice, Academic Press, Orlando, Fla. (1986); Current Protocols in Molecular Biolopy, F. M. Ausubel, et al. ed., Wiley Interscience, New York, (1987).

To prepare antibodies reactive with a protein of interest, the protein must be first enriched or purified. Relatively crude antigenic preparations of the protein may be used for immunization purposes. However, highly purified protein is required to determine accurately if hybridomas are producing the sought after monoclonal antibodies or to assay the antibody titers of immune serum.

Once the AAD-12 has been isolated, antibodies specific for AAD-12 may be raised by conventional methods that are well known in the art. Repeated injections into a host of choice over a period of weeks or months will elicit an immune response and result in significant anti-AAD-12 serum titers. Preferred hosts are mammalian species and more highly preferred species are rabbits, goats, sheep and mice. Blood drawn from such immunized animals may be processed by established methods to obtain antiserum (polyclonal antibodies) reactive with AAD-12. The antiserum may then be affinity purified by adsorption to AAD-12 according to techniques known in the art. Affinity purified antiserum may be further purified by isolating the immunoglobulin fraction within the antiserum using procedures known in the art. The resulting material will be a heterogeneous population of immunoglobulins reactive with AAD-12.

Anti-AAD-12 mAbs are readily prepared using purified AAD-12. Methods for producing mAbs have been practiced for several decades and are well known to those of ordinary skill in the art. Repeated intraperitoneal or subcutaneous injections of AAD-12 in adjuvant will elicit an immune response in most animals, especially mice. Hyperimmunized B-lymphocytes are removed from the animal and fused with a suitable fusion partner cell line capable of being cultured indefinitely. Numerous mammalian cell lines are suitable fusion partners for the production of hybridomas. Many such lines are commercially available from the ATCC and commercial suppliers.

Once fused, the resulting hybridomas are cultured in a selective growth medium for one to two weeks. Two well known selection systems are available for eliminating unfused myeloma cells or fusions between myeloma cells from the mixed hybridoma culture. The choice of selection system depends on the strain of mouse immunized and myeloma fusion partner used. The AAT selection system, described by Taggart and Samloff, Science 219, 1228 (1982), may be used; however, the HAT (hypoxanthine, aminopterin, thymidine) selection system, described by Littlefield, Science 145, 709 (1964), is preferred because of its compatibility with mouse cells and fusion partners mentioned above.

Spent growth medium is then screened for immunospecific mab secretion. Enzyme linked immunosorbant assay procedures are best suited for this purpose; though, radioimmune assays adapted for large volume screening are also acceptable. Multiple screens designed to consecutively pare down the considerable number of irrelevant or less desired cultures must be performed to isolate the small percentage of mAbs of the instant invention. Cultures that secrete mAbs reactive with AAD-12 were isotyped using commercially available assays.

Hybridoma cultures which secrete the sought-after anti AAD-12 mAbs should be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures must be re-assayed for antibody secretion and isotype to ensure that a stable antibody-secreting culture has been established.

The claimed anti-AAD-12 antibodies can be immobilized to a surface so that some of the antibody binding site remains exposed and capable of binding AAD-12. A wide assortment of schemes for immobilizing antibodies has developed over the past few decades. Immobilization can be accomplished by covalently coupling the antibody directly to the desired surface or by bridging the antibody to the surface.

CNBr and carbodiimide coupling of antibodies to polysaccharide based beads such as Sepharose® (Pharmacia, Pistcataway, N.J.) are illustrative of direct coupling schemes that are consistent with the invention. Direct couplings generally do not orient the antibodies in any particular fashion; however, some types of direct couplings are able to reproducibly orient the antibody on the immobilizing substance.

Preferred coupling schemes orient the antibody such that its antigen binding regions remain exposed. One such scheme utilizes the natural carbohydrate found on the heavy chains of the antibody. By first oxidizing the carbohydrate moieties to the corresponding aldehydes then reacting the aldehyde with a primary amino group on the surface, it is possible to link the antibody in an advantageous orientation.

Many types of bridges are possible and include small organic linkers which covalently bind the antibody to the immobilizing substance. Such spacer arms are acceptable and preferably should not interact with proteins once the bridge has been formed.

The above discussion is in no way meant to limit the scope of the invention. Numerous other well known schemes for linking antibodies to immobilizing substances are consistent with the invention.

It is well known that antibodies labeled with a reporting group can be used to identify the presence of antigens in a variety of milieus. Antibodies labeled with radioisotopes have been used for decades in radioimmune assays to identify, with great precision and sensitivity, the presence of antigens in a variety of biological fluids. More recently, enzyme labeled antibodies have been used as a substitute for radiolabeled antibodies in the popular ELISA.

Antibodies of the present invention can be bound to an immobilizing substance such as a polystyrene well or particle and used in immunoassays to determine whether AAD-12 is present in a test sample. In this embodiment of the invention, a sample is contacted with the immunoaffinity surface and allowed to incubate. After a washing step, any AAD-12 that has bound to the immunoaffinity surface is detected by contacting the surface with another antibody of the invention labeled with a reporting group.

The use of lateral flow strips or immunochromatographic strips with the claimed antibodies and assay methods is consistent with the invention. Lateral flow assays are well known in the art. See for example U.S. Pat. No. 6,485,982. In this mode lateral flow tests can be used for qualitative or semiquantitative detection of AAD-12 alone or simultaneously with other analytes. Lateral flow tests are the simplest to use of all the test formats described herein and are particularly useful in field settings where plant material is quickly extracted into a solution and tested on a lateral flow strip. In this mode it is only necessary to place the lateral flow strip into a liquid sample or to apply the liquid sample to the lateral flow strip and read the results after a predetermined time. All lateral flow tests should incorporate either a procedural control line or a sample control line that is used to validate the test result. Appearance of two lines, therefore, indicates a positive result, while a valid negative test produces only the control line. If only the test line appears, or if no lines appear, it is invalid.

A typical lateral flow test strip consists of four main components; a sample pad upon which the test sample is applied, a conjugate pad that contains antibodies of the present invention conjugated to colored particles (typically colloidal gold particles, or latex microspheres); a reaction membrane such as a hydrophobic nitrocellulose or cellulose acetate membrane onto which a different antibody of the invention is immobilised in a line across the membrane as a capture zone or test line; and, a waste reservoir designed to draw the sample across the reaction membrane by capillary action.

The components of the lateral flow strip are normally fixed to an inert backing material and may be presented in a simple dipstick format or within a plastic casing with a sample port and reaction window showing the capture and control zones.

In another mode of the assay embodiment, a test sample suspected of containing AAD-12 is dried onto a surface, forming an immobilized test sample. A labeled antibody of the invention is then contacted with the immobilized test sample and allowed to incubate. If the sample contains AAD-12, the labeled antibody will bind to the immobilized AAD-12. This method can also be done using an unlabeled antibody of the invention followed by a labeled secondary antibody that binds to an antibody of the invention which has already bound to AAD-12. After washing, the immobilized test sample is measured to detect the presence of any reporting groups.

Reporting groups are typically enzymes such as alkaline phosphatase, horseradish peroxidase or beta-D-galactosidase. Suitable substrates produce a color change when reacted with the enzyme. In so doing, measurements of the color intensity can be quantitated using a spectrophotometer. If the reporting group is a radioisotope, an appropriate gamma or beta ray detecting instrument can be used to quantitate the reporting group. The intensity of the reporting group directly correlates, with the amount of AAD-12 in the test sample.

The following examples will help describe how the invention is practiced and will illustrate the characteristics of the claimed anti-AAD-12 antibodies and assays.

Example 1

Immunogen Preparation

AAD-12 protein was extracted from lyophilized leaf tissue removed from transgenic soybean in a PBST (Phosphate Buffered Saline with 0.05% TWEEN™ 20, pH 7.4) based buffer with added stabilizers, and the soluble proteins were collected in the supernatant after centrifugation. The supernatant was filtered and the soluble proteins were allowed to bind to Phenyl Sepharose™ (PS) beads (GE Healthcare). After an hour of incubation, the PS beads were washed with PBST and the bound proteins were eluted with Milli-Q™ water. Sodium chloride was added to increase the conductivity and the PS purified proteins were loaded onto an anti-AAD-12 immunoaffinity column which had been conjugated with an AAD-12 specific polyclonal antibody raised against recombinant AAD-12 produced in *Pseudomonas fluorescens*. The non-bound proteins were collected from the column and the column was washed extensively with pre-chilled PBS (phosphate buffered saline, pH 7.4). The bound proteins were eluted from the column with a 3.5 M NaSCN, 50 mM Tris™, pH 8.0 buffer. Microbial-derived AAD-12 and soybean-derived AAD-12 were examined by SDS-PAGE and western blotting.

In the microbe-derived AAD-12, the major protein band, as visualized on the Coomassie stained SDS-PAGE gel, was approximately 32 kDa. As expected, the corresponding plant-derived AAD-12 protein was identical in size to the microbe-derived protein. Predictably, the plant purified fractions contained a minor amount of non-immunoreactive impurities in addition to the AAD-12 protein. The co-purified proteins were likely retained on the column by weak interactions with the column matrix.

The microbe-derived AAD-12 and plant-derived extract showed a positive signal of the expected size on the western blot using anti-AAD-12 polyclonal antibody. In the AAD-12 western blot analysis, no immunoreactive proteins were observed in negative control (native soybean) extract and no alternate size proteins (aggregates or degradation products) were seen in the samples from the transgenic plant.

Example 2

Hybridoma Preparation

Mice were immunized with purified AAD-12, and standard fusion techniques were used to prepare a panel of hydridomas expressing anti AAD-12 monoclonal antibodies. Samples of spent tissue culture media were removed aseptically from each well containing a hybridoma culture and assayed for AAD-12 reactivity using the following antibody capture ELISA method. Microtiter wells were coated with a solution of 1-10 μg/mL of purified AAD-12. The wells were washed and samples of spent tissue media were placed in the wells and allowed to incubate. The wells were washed and horseradish peroxidase-labeled goat anti mouse antiserum was added and allowed to incubate. The plates were washed, substrate was added to develop a color reaction and the plates were read for OD (optical density). Wells with high OD readings were mapped back to culture wells containing the hybridomas. The AAD-12 antibody positive cultures were continually screened for antibody production to assure growth stability and antibody production as the cultures were expanded. Several rounds of limiting dilution cloning were performed to establish true monoclonality for each culture. Further assays on antibody positive clones were conducted to determine the suitability of each antibody for use in the presently claimed quantitative detection methods for field use with plant material.

Example 3

Quantitative ELISA

This example is a method for the quantitative determination of AAD-12 in soybean tissues using antibodies and methods of the claimed invention. The calibration standard curve quantitative range is from 0.25 ng/mL to 10 ng/mL in buffer. The AAD-12 protein level in soybean seed, leaf (V5 and V10), root, and forage at R3 stages can be determined with a limit of quantitation (LOQ) of 1.0 ng/mg and a limit of detection (LOD) of 0.5 ng/mg.

Test substances were representative soybean tissue samples which were genetically modified to express the AAD-12 protein, and non-transgenic control soybean of the variety Maverick. The tissues, listed below, were collected from the greenhouse.

List of Non-Transgenic Soybean Samples

| Sample Group No. | Tissue | Sample Description |
| --- | --- | --- |
| 081008-001-0001 | Forage (Whole plant; leaf and stem; R3) | non-transgenic control |
| 081008-004-0001 | Root (R3) | non-transgenic control |
| 081008-009-0001 | Seed | non-transgenic control |
| 081008-010-0001 | Leaves (V5) | non-transgenic control |
| 081008-011-0001 | Leaves (V10) | non-transgenic control |

List of Transgenic Soybean Samples

| Sample Group No. | Tissue | Description |
| --- | --- | --- |
| 081008-003-0001 | Forage (Whole Plant; leaf and stem; R3) | AAD-12 |
| 081008-006-0001 | Root | AAD-12 |
| 081008-007-0001 | Leaves (R7) | AAD-12 |
| 081008-012-0001 | Seed | AAD-12 |
| 081008-013-0001 | Leaves (V5) | AAD-12 |
| 081008-014-0001 | Leaves (V10) | AAD-12 |

The reference substances below employed in this study were a purified AAD-12 protein used as a calibration standard and as fortification material in the ELISA analysis, a purified AAD-12 protein, and a purified AAD-12 protein used to test for cross reactivity.

| Protein | Test Substance Number | Purity or Concentration | Reference |
| --- | --- | --- | --- |
| Cry1F | 104301 | 0.164 mg/mL | BIOT033236 |
| AAD-1 | 105930 | 0.1805 mg/mL | BIOT09-203007 |
| Cry1Ac | 102337 | 0.26 mg/mL | BIOT08-162946 |
| AAD-12 | 030732 | 0.2 mg/mL | BIOT09-203009 |
| PAT | 105742 | 0.3 mg/mL | BIOT063302 |
| Cry35Ab1 | 104066 | 0.128 mg/mL | BIOT08-162948 |
| Cry34Ab1 | 104874 | 0.248 mg/mL | BIOT09-203014 |

All test and reference substances were stored in temperature monitored freezers, and removed only for sample preparation and analysis. Briefly, the AAD-12 protein was extracted from soybean samples (V5, V10, forage, and root) with PBST (phosphate buffered saline solution containing 0.05% Tween™ 20) buffer with 0.75% ovalbumin (OVA) (PBST/OVA). The AAD-12 protein was extracted from soybean seeds with a PBS solution containing 0.05% Tween™ 20 (PBST) and 0.1% Triton™ X-100. The extract was centrifuged, and the aqueous supernatant was collected, diluted and assayed using a specific AAD-12 ELISA. An aliquot of the diluted sample was incubated with enzyme-conjugated anti-AAD-12 monoclonal 539B470.2 antibody in the wells of an anti-AAD-12 polyclonal antibody coated plate in a sandwich ELISA format. Both antibodies in the sandwich pair captured AAD-12 in the sample. At the end of the incubation period, the unbound reagents were removed from the plate by washing with PBST. The presence of AAD-12 was detected by incubating the antibody-bound enzyme conjugate with an enzyme substrate, generating a colored product. Since the AAD-12 was bound in the antibody sandwich, the level of color development was proportional to the concentration of AAD-12 in the sample (i.e., lower protein concentrations result in lower color development). The color reaction was stopped by adding an acidic solution and the absorbance at 450 nm minus absorbance at 650 nm was measured using a plate reader. A calibration curve was estimated from the 7 standard concentrations using a quadratic regression equation with a coefficient of determination of >0.990. This AAD-12 ELISA was highly specific for the quantitation of AAD-12 protein.

Example 4

Assay Validation

The preliminary quantitative range for the method was established independently during method development and a pre-validation study. The standard concentrations provided the lowest mean percent errors for the given concentration points. The limit of detection (LOD) and limit of quantitation (LOQ) for the determination of AAD-12 in each tissue were empirically defined on the basis of assay parameters (absorbance, background, and linear range), matrix interferences and/or doses constituting the standard curve. They were also supported by statistical approaches following the method of Keith et al. (Keith, L. H., Crummett, W., Deegan, J., Jr., Libby, R. A., Taylor, J. K., Wentler, G. 1983. Principles of Environmental Analysis, *Anal. Chem.*, 55, 2210-2218) and by testing each control sample fortified with 5 ng/mL (0.5 ng/mg) of AAD-12 protein.

The cross-reactivity of this AAD-12 ELISA to non-target proteins Cry1F, Cry1Ac, Cry34Ab1, Cry35Ab1, PAT and AAD-1 was tested in this study. These proteins were prepared at concentrations of 1 µg/mL and 10 µg/mL in PBST/OVA. On the same plate, an AAD-12 standard curve was generated as a reference. The OD response for the non-target proteins was interpolated from the AAD-12 standard curve and percent cross-reactivity was calculated using the following formula, % cross-reactivity=100×(measured conc. by AAD-1.2 std curve/theoretical conc. of target protein).

Sample extracts (matrix) for each soybean tissue (1×, 5× and 10× dilutions) of negative control were spiked with different concentrations to create standard curves. The matrix-spiked standard curves were interpolated from a non-spiked standard curve run on the same plate. A difference of greater than 15% between the observed (a non-spiked standard curve used to interpolate the matrix-spiked standard concentrations) and theoretical (concentration of the matrix-spiked standard curve) means for each standard concentration level was considered indicative of a potential matrix effect.

A series of five extractions were performed on transgenic soybean tissues known to express AAD-12. Briefly, 1.5 mL of buffer was added to the tissue sample (15 mg) and extracted as described above. Following extraction and centrifugation, the extracted solution was removed by pipette. After the first extract, an aliquot of 200 µL of buffer was added and mixed with the sample, centrifuged and the supernatant removed and added to the first extraction solution. Another 1.5 mL of buffer was added to the tissue, and the extraction process was repeated. This procedure was repeated three more times to obtain 5 consecutive extractions. The concentration of AAD-12 in each extraction was determined using the AAD-12 ELISA. At least five replicates were studied for each tissue sample. The apparent efficiency of the tissue extraction process was determined by comparison of the AAD-12 protein in the first extract relative to the total AAD-12 protein in all five extracts.

The accuracy of the method was determined by measuring the recovery of the AAD-12 protein from negative control matrices spiked with low (0.5 ng/mg DW), midpoint (1, and 4 ng/mg DW) and high (8 ng/mg DW) levels of AAD-12 protein. A minimum of five replications for each concentration was analyzed. The accuracy of the assay was indicated as percent of recovery. Recoveries between 67-120% were considered acceptable.

The precision of the method was determined using the results of fortified soybean control samples analyzed by two analysts on multiple days. The control sample extracts were fortified with three levels of AAD-12 standard (0.25 ng/mg, 0.5 ng/mg, 4 ng/mg and 8 ng/mg). Each level of fortified extract was run in triplicate on each ELISA plate. The mean recovery concentration, standard deviation (stdev), and percent coefficient of variation (% CV) were calculated for each of the samples.

Positive samples (V5 leaf and forage (whole plant)) were tested for precision as well. The mean predicted concentration, standard deviation (stdev), and percent coefficient of variation (% CV) were calculated for each sample. Within and across day precision were calculated.

The purpose of this experiment was to verify that the AAD-12 protein standard and the AAD-12 protein in plant extracts exhibited a similar overall response in the ELISA. This was done for all transgenic tissues by assessing the agreement of the results from the dilution of a single extract interpolated from the quantitative range of the standard curve. The coefficient of variation for the interpolated results from all quantifiable dilutions was calculated for each tissue type.

Seed, leaf, forage (whole plant) and root tissues were tested for false-positive and false-negative occurrences. Fifteen unfortified control samples and fifteen samples fortified at 0.25 ng/mg were analyzed for each tissue to determine false-positive and false-negative rates. A false-positive result occurs when residue at or above the established LOD is found in a sample known to be free of analytes. A false negative occurs when no residue is detected in a sample fortified at the LOD.

ELISA readings were recorded from a Molecular Dynamics Microplate Reader using SOFTmax PRO software program. Concentration data were transferred to SAS, JMP or Microsoft Excel for calculations of mean, percent error, statistical mean, standard deviation, and % CV.

The limit of detection (LOD) of an immunoassay is defined as the analyte concentration that gives a response which has a statistically significant difference from the response of a zero analyte sample. The limit of quantitation (LOQ), or the working range of an assay, is generally defined as the highest and lowest concentrations which can be determined with an acceptable degree of precision. In this study, the targeted LOD and LOQ for the determination of AAD-12 in each tissue were empirically defined on the basis of assay parameters (such as absorbance, background, signal-to-noise ratio, and linear range), matrix interferences, and the standard curve concentrations. The LOD and LOQ were also determined by standard statistical approaches. Following established guidelines, the LOD and LOQ were calculated using the standard deviation from the 0.5 ng/mg recovery results. The LOQ was calculated as ten times the standard deviation (10s), and the LOD was calculated as three times the standard deviation (3s) of the results of the analysis of a minimum of 5 samples per matrix. The calculated results and target LODs and LOQs for each tissue are summarized in the table below.

Summary of LOD and LOQ Calculation of AAD-12
ELISA in Soybean Tissue

| Tissue | Spiked Level ng/mg | Average Recovery ng/mg | Standard Deviations s | 3 × s | Target LOD ng/mg | 10 × s | Target LOQ ng/mg |
|---|---|---|---|---|---|---|---|
| Forage (Whole Plant) | 0.5 | 0.29 | 0.06 | 0.18 | 0.5 | 0.60 | 1.0 |
| Root | 0.5 | 0.30 | 0.05 | 0.15 | 0.5 | 0.50 | 1.0 |
| V5 Leaf | 0.5 | 0.32 | 0.05 | 0.15 | 0.5 | 0.50 | 1.0 |
| Seed | 0.5 | 0.36 | 0.03 | 0.03 | 0.5 | 0.10 | 1.0 |
| V10 Leaf | 0.5 | 0.46 | 0.03 | 0.03 | 0.5 | 0.10 | 1.0 |

The target LOD is 0.5 ng/mg for all soybean matrices. The target LOQ is 1.0 ng/mg for all soybean matrices.

Several relevant proteins such as Cry1F, Cry1Ac, Cry34Ab1, Cry35Ab1, PAT, and AAD-1 were tested for cross reactivity. No cross reactivity was observed at the concentrations tested for these proteins (10,000 ng/mL).

The results of the matrix tests are summarized in the following table.

Summary of Matrix Effects

| Tissue | SGN# | Matrix Dilution[a] | | | Lowest dilution w/o matrix effect |
|---|---|---|---|---|---|
| | | 1X | 5X | 10X | |
| V5 Leaf | 081008-010-0001 | Yes | No | No | 1:5 |
| V10-12 Leaf | 081008-011-0001 | Yes | No | No | 1:5 |
| R3 Forage (whole plant) | 081008-001-0001 | Yes | No | No | 1:5 |
| R3 Root | 081008-004-0001 | No | No | No | 1:2 |
| R8 Seed | 081008-009-0001 | Yes | Yes | No | 1:10 |

"Yes" represented that a standard curve is affected by matrix when the mean percent error between the observed and theoretical values for all the seven standard concentration levels is greater than 15%. "No" represented that no matrix effects or the mean percent error between the observed and theoretical values for all the seven standard concentration levels is less than 15%.

A difference of greater than 15% between the observed and theoretical means for any of the seven standard concentration levels was considered indicative of a matrix effect. No matrix effect was observed in root at the 1× spiked-matrix level. No matrix effects were found at the 5× spiked-matrix level for V5 leaf, V10 leaf, forage (whole plant). However, matrix effects were found in seed at the 5× level. For AAD-12 quantification in soybean tissues, at least 2× dilution is recommended for root; at least 5× dilution is recommended for V5 leaf, V10 leaf and forage; and at least 10× dilution is recommended for seed.

Determining total AAD-12 protein levels in a sample is critical for examining extraction efficiency. Positive samples were extracted with extraction buffer five consecutive times and the AAD-12 protein concentration in each extract was determined by ELISA. The apparent extraction efficiency was based on the amount of AAD-12 protein in the first extraction relative to the total amount of AAD-12 in all five extractions. The extraction efficiencies of the AAD-12 protein from soybean tissues are shown in the table below.

Summary of Extraction Efficiency of AAD-12 from Soybean Tissue

| Sample | SGN# | Mean Extraction Efficiency (%) | Standard Deviation | CV % | % EE Range |
|---|---|---|---|---|---|
| Forage (Whole Plant) | 081008-003-0001 | 93.7 | 1.1 | 1.1 | 92.3-95.2 |
| Root | 081008-006-0001 | 90.0 | 0.4 | 0.5 | 89.6-90.6 |
| V5 Leaf | 081008-013-0001 | 97.2 | 0.2 | 0.3 | 96.9-97.6 |
| Seed | 081008-012-0001 | 85.8 | 5.6 | 6.6 | 79.1-91.1 |
| V10 Leaf | 081008-014-0001 | 93.3 | 1.4 | 1.5 | 91.1-94.7 |

The extraction efficiencies for forage (whole plant), root, seed, V5 leaf and V10 leaf ranged from 85.8-97.2%.

The mean recovery levels of AAD-12 from all tissues when fortified at levels equating to the LOQ, mid- and high-points of the standard curve are shown in the table below.

Summary of Accuracy Results

| Matrix | Fortification Level | | Recovery Rate (%) | | | |
|---|---|---|---|---|---|---|
| | ng/mg | ng/mL[a] | Mean | Range | CV % | n |
| Forage (Whole Plant) | 8 | 80 | 71 | 59-77 | 9.4 | 5 |
| | 4 | 40 | 70 | 60-79 | 9.5 | 5 |
| | 1 | 10 | 67 | 57-76 | 10.3 | 5 |
| | 0.5 | 5 | 58 | 46-77 | 15.8 | 5 |
| | 0.5-8 | 5-80 | 66 | 46-79 | 14.4 | 20 |
| Root | 8 | 80 | 72 | 66-77 | 6.0 | 5 |
| | 4 | 40 | 71 | 64-76 | 6.2 | 5 |
| | 1 | 10 | 69 | 62-76 | 7.9 | 5 |
| | 0.5 | 5 | 61 | 51-76 | 13.0 | 5 |
| | 0.5-8 | 5-80 | 68 | 51-77 | 11.1 | 20 |
| Leaf V5 | 8 | 80 | 75 | 66-80 | 7.4 | 5 |
| | 4 | 40 | 76 | 67-83 | 8.6 | 5 |
| | 1 | 10 | 73 | 66-82 | 7.8 | 5 |
| | 0.5 | 5 | 65 | 53-78 | 12.9 | 5 |
| | 0.5-8 | 5-80 | 72 | 53-83 | 11.2 | 20 |
| Seed | 8 | 80 | 75 | 72-77 | 2.4 | 5 |
| | 4 | 40 | 75 | 74-77 | 1.6 | 5 |
| | 1 | 10 | 74 | 72-76 | 2.4 | 5 |
| | 0.5 | 5 | 73 | 71-75 | 2.6 | 5 |
| | 0.5-8 | 5-80 | 74 | 71-77 | 2.4 | 20 |
| Leaf V10 | 8 | 80 | 99 | 97-101 | 1.8 | 5 |
| | 4 | 40 | 100 | 92-105 | 5.2 | 5 |
| | 1 | 10 | 96 | 94-99 | 2.8 | 5 |

-continued

| Matrix | Fortification Level | | Recovery Rate (%) | | | |
|---|---|---|---|---|---|---|
| | ng/mg | ng/mL[a] | Mean | Range | CV % | n |
| | 0.5 | 5 | 93 | 91-94 | 1.4 | 5 |
| | 0.5-8 | 5-80 | 97 | 91-105 | 4.3 | 20 |

[a]Samples were diluted 10X prior to analysis.

Spiked at the LOQ level or above, V5 leaf, V10 leaf and seed were 67-100% within the 67-120% specification for the mean recovery with percent coefficient of variances (% CVs) at or below 16%.

The assay precision and ruggedness were examined using V5 leaf and forage (whole plant) extracts containing four levels of AAD-12 protein. The levels were 8 ng/mg, 4 ng/mg, 0.5 ng/mg and 0.25 ng/mg. The intra-day precision of the assay was less than or equal to 6.3%, 10.8%, 9.6% and 15.0% for the V5 leaf extract fortified at 8, 4, 0.05 and 0.25 ng/mg, respectively. The intra-day precision of the assay was less than or equal to 3.5%, 13.1%, 10.1% and 10.9% for the forage (whole plant) extract fortified at 8, 4, 0.5 and 0.25 ng/mg, respectively. Positive V5 leaf and forage samples were also tested for assay ruggedness. The intra-day precision of the assay was less than or equal to 9.7% and 19.7% for the V5 leaf and whole plant, respectively.

The inter-assay precision across all days and analysts was 4.6%, 10.1%, 6.4% and 12.9% for the V5 leaf extracts fortified at 8, 4, 0.5 and 0.25 ng/mg, respectively. The inter-assay precision across all days and analysts was 6.0%, 10.5%, 6.4% and 10.1% for the forage extracts fortified at 8, 4, 0.5 and 0.25 ng/mg, respectively. The inter-assay ruggedness across days and analysts was 11.3% and 14.1% for positive V5 leaf and forage, respectively.

Equivalence of standard and test substance response in the AAD-12 ELISA was demonstrated using up to eight serial dilutions of extracts from AAD-12 positive tissues. For each tissue extract, five or more of the dilutions fell with in the quantitative range of the standard curve, and the % CV of the quantified results was less than 20%.

Unfortified control samples (matrix blanks) and samples fortified at 0.25 ng/mg (LOD=0.5 ng/mg) were analyzed to determine the false-positive and false-negative rate. There were no false positives from the unfortified control samples and no false negatives reported from the LOD fortified samples analyzed in this study.

In summary, the method was validated over the concentration range of 1.0 to 8.0 ng/mg dry weight (DW) and has a validated limit of quantitation (LOQ) in all soybean tissues of 1.0 ng/mg DW and a limit of detection (LOD) in all soybean tissue of 0.5 ng/mg DW. The AAD-12 protein was recovered at acceptable levels from all tissues. The validated assay is specific for AAD-12 protein when compared to the non-target proteins tested in previous studies. For AAD-12 protein quantification in soybean tissues, a 2× or greater dilution is recommended for root, a 5× or greater dilution is recommended for V5 leaf, V10 leaf and forage, and a 10× or greater dilution is recommended for seed. In addition, AAD-12 protein was efficiently extracted from all soybean tissues. The assay was shown to have acceptable accuracy and precision, and no false-positive or false-negative results were seen below the target LOD. This AAD-12 ELISA method has been demonstrated to be suitable for quantitative measurements of the AAD-12 protein in soybean tissue.

What is claimed is:

1. An isolated monoclonal antibody that specifically binds to aryloxyalkanoate dioxygenase-12 enzyme (AAD-12), wherein the monoclonal antibody is produced by a hybridoma having an American Type Culture Collection (ATCC) Accession Number selected from the group consisting of PTA-10919, PTA-10920, PTA-10921, PTA-10922, and PTA-10923.

2. The monoclonal antibody of claim 1 produced by the hybridoma having ATCC Accession Number PTA-10919.

3. The monoclonal antibody of claim 1 produced by the hybridoma having ATCC Accession Number PTA-10920.

4. The monoclonal antibody of claim 1 produced by the hybridoma having ATCC Accession Number PTA-10921.

5. The monoclonal antibody of claim 1 produced by the hybridoma having ATCC Accession Number PTA-10922.

6. The monoclonal antibody of claim 1 produced by the hybridoma having ATCC Accession Number PTA-10923.

7. A hybridoma cell line that produces a monoclonal antibody of claim 1 that is on deposit with the American Type Culture Collection (ATCC) under Accession Numbers selected from the group consisting of PTA-10919, PTA-10920, PTA-10921, PTA-10922, and PTA-10923.

8. The hybridoma cell line of claim 7 deposited under ATCC Accession Number PTA-10919.

9. The hybridoma cell line of claim 7 deposited under ATCC Accession Number PTA-10920.

10. The hybridoma cell line of claim 7 deposited under ATCC Accession Number PTA-10921.

11. The hybridoma cell line of claim 7 deposited under ATCC Accession Number PTA-10922.

12. The hybridoma cell line of claim 7 deposited under ATCC Accession Number PTA-10923.

13. A method for identifying the presence of AAD-12 enzyme comprising:
 a) immobilizing a first monoclonal antibody of claim 1 onto an assay surface, and then washing said assay surface;
 b) contacting said assay surface with a liquid suspected of containing AAD-12 for a period of time sufficient to allow binding, and then washing said assay surface;
 c) contacting said assay surface with a different second antibody of claim 1 conjugated to a reporting group for a period of time sufficient to allow binding of said second conjugated monoclonal antibody, and then washing said assay surface; and,
 d) detecting the presence or absence of said reporting group, wherein the presence of said reporting group indicates the presence of AAD-12 in the liquid.

14. A method for the quantitative determination of AAD-12 enzyme comprising:
 a) immobilizing an AAD-12 antiserum onto an assay surface;
 b) contacting said assay surface with a liquid suspected of containing AAD-12 for a period of time sufficient to allow binding then washing said assay surface;
 c) contacting said assay surface with a monoclonal antibody of claim 1 conjugated to a reporting group for a period of time sufficient to allow binding of said second conjugated monoclonal antibody, and then washing said assay surface; and,
 d) quantitating the presence of said reporting group by comparison to a calibration curve, wherein the presence of said reporting group indicates the presence of AAD-12 in the liquid.

15. The method of claim 14 wherein the conjugated monoclonal antibody is produced by the hybridoma having ATCC Accession Number PTA-10920.

\* \* \* \* \*

UNITED STATES PATENT AND TRADEMARK OFFICE
CERTIFICATE OF CORRECTION

PATENT NO. : 8,460,891 B2  
APPLICATION NO. : 13/151389  
DATED : June 11, 2013  
INVENTOR(S) : Guomin Shan et al.

Page 1 of 1

It is certified that error appears in the above-identified patent and that said Letters Patent is hereby corrected as shown below:

In the Specification

<u>Column 9,</u>  
Line 42, "by AAD-1.2" should read --by AAD-12--.

Signed and Sealed this  
Twenty-sixth Day of November, 2013

Margaret A. Focarino  
*Commissioner for Patents of the United States Patent and Trademark Office*